(12) United States Patent
Stoddart et al.

(10) Patent No.: US 9,815,764 B2
(45) Date of Patent: Nov. 14, 2017

(54) HOMOCHIRAL METAL-ORGANIC FRAMEWORK WITH ENANTIOPURE PILLAR[5]ARENE ACTIVE DOMAINS

(71) Applicants: Northwestern University, Evanston, IL (US); King Abdulaziz City for Science and Technology (KACST), Riyadhh (SA)

(72) Inventors: James Fraser Stoddart, Evanston, IL (US); Nathan Strutt, Portland, OR (US)

(73) Assignees: NORTHWESTERN UNIVERSITY, Evanston, IL (US); KING ABDULAZIZ CITY FOR SCIENCE AND TECHNOLOGY (KACST) (SA)

( * ) Notice: Subject to any disclaimer, the term of this patent is extended or adjusted under 35 U.S.C. 154(b) by 0 days.

(21) Appl. No.: 14/844,708

(22) Filed: Sep. 3, 2015

(65) Prior Publication Data

US 2016/0060201 A1    Mar. 3, 2016

Related U.S. Application Data

(60) Provisional application No. 62/045,514, filed on Sep. 3, 2014.

(51) Int. Cl.
| | |
|---|---|
| *C07C 29/00* | (2006.01) |
| *C07C 65/24* | (2006.01) |
| *C07C 51/487* | (2006.01) |
| *C07F 3/00* | (2006.01) |

(52) U.S. Cl.
CPC ............ *C07C 65/24* (2013.01); *C07C 51/487* (2013.01); *C07F 3/003* (2013.01); *C07B 2200/07* (2013.01); *C07C 2603/92* (2017.05)

(58) Field of Classification Search
CPC ........ C07F 3/003; C07C 65/24; C07C 51/487
USPC ........................... 556/118, 131, 132; 562/466
See application file for complete search history.

(56) References Cited

U.S. PATENT DOCUMENTS

| | | | |
|---|---|---|---|
| 7,906,096 B2 | 3/2011 | Bae et al. | |
| 2013/0210157 A1 | 8/2013 | Chen et al. | |

FOREIGN PATENT DOCUMENTS

| | | |
|---|---|---|
| CN | 102911071 A | 2/2013 |
| CN | 103193831 A | 7/2013 |
| CN | 103331151 A | 10/2013 |
| CN | 103396298 A | 11/2013 |
| CN | 103551118 A | 2/2014 |
| WO | 2009149381 A2 | 12/2009 |

OTHER PUBLICATIONS

Strutt et al., J. Am. Chem. Soc., vol. 134, pp. 17436-17439 (2012).*
Gallardo et al., "Songoshira Coupling Applied in the Synthesis of 1,2,4-Oxadiazole-Based Nonsymmetrical Liquid Crystals," Synthesis 4:605-609 (2008).
Li et al., "Docking in Metal-Organic Frameworks," Science 325:855-859 (2009).
Ogoshi et al., "para-Bridged Symmetrical Pillar[5]arenes: Their Lewis Acid Catalyzed Synthesis and Host-Guest Property," J. Am. Chem. Soc. 130:5022-5023 (2008).
Strutt et al., "Incorporation of an A1/A2-difunctionalized pillar[5]arene into a metal-organic framework," J. Am. Chem. Soc. 134:17436-9 (2012).
Strutt et al., "Enantiopure pillar[5]arene active domains within a homochiral metal-organic framework," Chem Commun (Camb) 50:7455-8 (2014).
Valente et al., "Metal-organic frameworks with designed chiral recognition sites," Chem. Commun. 46:4911-4913 (2010).

* cited by examiner

*Primary Examiner* — Pancham Bakshi
(74) *Attorney, Agent, or Firm* — Klintworth & Rozenblat IP LLP (57) ABSTRACT

Homochiral metal organic framework (MOF) selected from a group consisting of $(S_p)$-P5A-MOF-1 and $(R_p)$-P5A-MOF-1 is provided. The homochiral MOFs are prepared from pure enantiomer struts of formula (I):

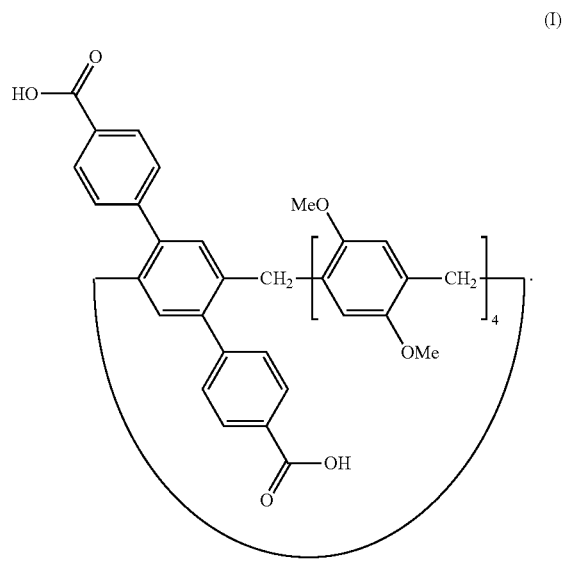

The homochiral MOFs are suitable for separation of enantiomers from racemic mixtures.

9 Claims, 9 Drawing Sheets

(9 of 9 Drawing Sheet(s) Filed in Color)

(Prior Art)

FIG. 3A $(SSR_p)$-4   $(SSS_p)$-4

HOMOCHIRAL METAL-ORGANIC FRAMEWORK WITH ENANTIOPURE PILLAR[5]ARENE ACTIVE DOMAINS

CROSS-REFERENCE TO RELATED APPLICATIONS

This application claims benefit of priority under 35 U.S.C. 119 to U.S. provisional patent application Ser. No. 62/045,514, filed Sep. 3, 2014, and entitled "A HOMOCHIRAL METAL-ORGANIC FRAMEWORK WITH ENANTIOPURE PILLAR[5]ARENE ACTIVE DOMAINS," the contents of which are herein incorporated by reference in its entirety.

STATEMENT REGARDING FEDERALLY SPONSORED RESEARCH OR DEVELOPMENT

This invention was made with government support under CHE-0924620 and DGE-0824162 awarded by the National Science Foundation. The government has certain rights in the invention.

BACKGROUND

1. Technical Field

The present disclosure relates to methods for preparing metal-organic frameworks for the separation of enantiomers from racemic mixtures.

2. Description of Related Art

Figure 1:
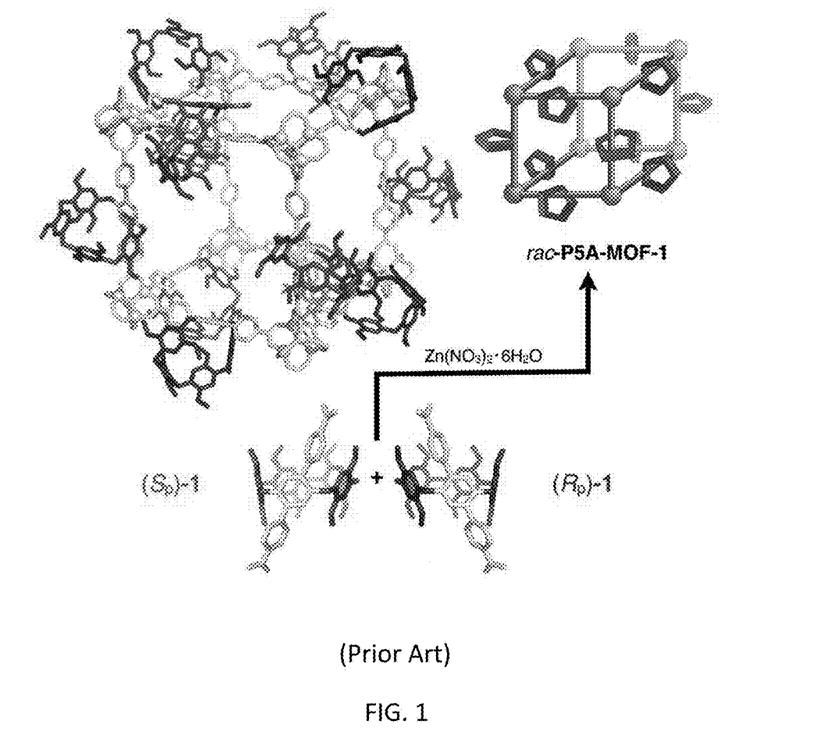
FIG. 1 depicts an exemplary synthesis route for rac-P5A-MOF-1 from the organic strut rac-1, wherein the ($S_p$)-1 (red) and ($R_p$)-1 (blue) are depicted.

Pillar[n]arenes are macrocycles composed of n hydroquinone rings connected through their para-positions by methylene bridges. These compounds are a new family of cavitands that have quickly become important players in the field of host-guest chemistry. As a result of their novel structures and the tunability of their pendant functional groups, pillar[n]arenes have been incorporated into many types of materials including polymers, nanoparticles and liquid crystals. Stoddart and coworkers described the incorporation of a rigid A1/A2-difunctionalized pillar[5]arene strut rac-1 (FIG. 1) into the metal-organic framework (MOF) rac-P5A-MOF-1 (N. L. Strutt et al., *J. Am. Chem. Soc.*, 2012, 134:17436). The pillar[5]arene cavities in rac-P5A-MOF-1 served to create active domains within the porous framework wherein an ordered distribution of guests can be maintained through highly specific charge-transfer interactions between the π electron-rich pillar[5]arene hosts and electron-poor guests. These active domains have the ability to take up large amounts of pyridinium cations and p-dinitrobenzene, and the pillar[5]arenes were demonstrated to be selective towards guests that are more electron deficient.

The substituents present in the pillar[n]arenes oblige them to exhibit planar chirality. In 1,4-dimethoxy-pillar[5]arene (DMpillar[5]arene), there are five planes of chirality that are coplanar with the 1,4-dimethoxybenzene rings and the two contiguous methylene carbons at the 2/5 ring positions. The chiralities in the two lowest energy enantiomeric conformational isomers of DMpillar[5]arene can be described with Cahn-Ingold-Prelog nomenclature as $R_pR_pR_pR_pR_p$ and $S_pS_pS_pS_pS_p$ that are abbreviated herein as $R_p$ and $S_p$, respectively. The $R_p$ and $S_p$ conformational isomers rapidly equilibrate as a result of ring rotations at room temperature, making it impossible to isolate an enantiomerically enriched sample of DMpillar[5]arene. The rate of the inversion process can be curtailed in pillar[n]arene derivatives such as in A1/A2-dihydroxypillar[5]arene and arrested completely in some derivatives, such as pillar[5]arenes with bulky substituents or pillar[5]arenes constituting mechanically interlocked compounds.

A racemic mixture of the organic strut rac-1, which cannot undergo stereochemical inversion on account of its rigid difunctionalization, was connected through $Zn_4O$ secondary building units (SBUs) to create rac-P5A-MOF-1 (Strutt et al. (2012)). The active domains in this MOF consist of pillar[5]arene recognition sites with randomly distributed chiralities.

Although there have been many known examples of homochiral MOFs with components that have either stereogenic centers or axes of chirality, the incorporation of planar chirality into homochiral MOFs is a relatively unexplored phenomenon. Porous frameworks, which contain enantiopure active domains, are also an area of interest as a result of their potential application as highly engineered chiral stationary phases for carrying out the separation of enantiomers by high-performance liquid chromatography (HPLC).

The methyl ester of strut rac-1 can be resolved on the analytical scale by chiral HPLC (Strutt et al. (2012)). In order to produce homochiral versions of P5A-MOF-1 and assess the porous frameworks for their ability to separate small molecule racemates, rac-1 must be resolved on a larger scale. While preparative scale chiral HPLC would likely be suitable for the resolution of rac-1, the technique is cost-prohibitive and not widely available.

BRIEF SUMMARY

In a first aspect, a homochiral metal organic framework (MOF) is provided. The homochiral MOF selected from a group consisting of $(S_p)$-P5A-MOF-1 and $(R_p)$-P5A-MOF-1.

In a second aspect, a method of preparing a homochiral metal organic framework (MOF) consisting of $(S_p)$-P5A-MOF-1 is provided. The method includes two steps. The first step includes preparing a mixture of $(S_p)$-1 and $Zn(NO_3)_2$ in a solvent, wherein $(S_p)$-1 is the $S_p$-enantiomer structure of formula (I):

(I)

The second step includes heating the mixture at an elevated temperature to form the homochiral metal organic framework (MOF) consisting of ($S_p$)-P5A-MOF-1.

In a third aspect, a method of preparing a homochiral metal organic framework (MOF) consisting of ($R_p$)-P5A-MOF-1 is provided. The method includes two steps. The first step includes preparing a mixture of ($R_p$)-1 and $Zn(NO_3)_2$ in a solvent, wherein ($R_p$)-1 is the $R_p$-enantiomer structure of formula (I):

(I)

The second step includes heating the mixture at an elevated temperature to form the homochiral metal organic framework (MOF) consisting of ($R_p$)-P5A-MOF-1.

In a fourth aspect, a method of preparing a pure enantiomer structure of formula (I) is provided:

(I)

The method includes two steps. The first step includes preparing a mixture comprising an aqueous-base solution and a solvent comprising a pure enantiomer structure of formula (II):

(II)

The second step includes heating the mixture at an elevated temperature to form the pure enantiomer structure of formula (I).

In a fifth aspect, a method of isolating an enantiomer compound from a racemic mixture is provided. The method includes two steps. The first step includes contacting the racemic mixture with a homochiral metal organic framework (MOF) selected from a group consisting of ($S_p$)-P5A-MOF-1 and ($R_p$)-P5A-MOF-1 to form a complex comprising the enantiomer compound and the homochiral MOF. The second step includes washing the complex with a solvent to remove an uncomplexed component of the racemic mixture.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features, objects and advantages other than those set forth above will become more readily apparent when consideration is given to the detailed description below. Such detailed description makes reference to the following drawings.

While the present invention is amenable to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments and claims herein for interpreting the scope of the invention.

DETAILED DESCRIPTION

The compositions and methods now will be described more fully hereinafter with reference to the accompanying drawings, in which some, but not all permutations and variations of embodiments of the invention are shown. Indeed, the invention may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

Overview

Figure 2:
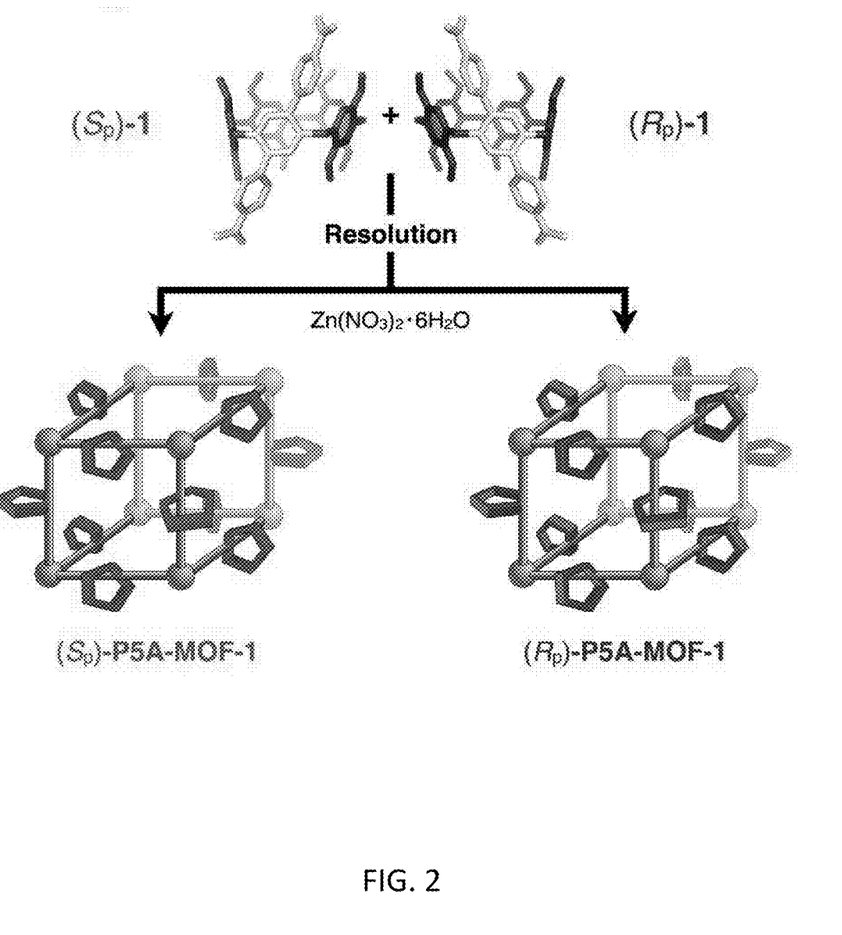
FIG. 2 depicts exemplary synthesis routes for homochiral ($S_p$)-P5A-MOF-1 and ($R_p$)-P5A-MOF-1 after the organic strut rac-1 is resolved to give ($S_p$)-1 (red) and ($R_p$)-1 (blue).

Applicants developed a method to resolve rac-1 that would be operable on the gram scale without the use of chiral chromatography. The enantiomers $(S_p)$-1 and $(R_p)$-1 can be functionalized with an enantiomerically pure chiral auxiliary, thereby converting the enantiomers into two diastereoisomers that can then be separated using normal phase chromatography. After separation, the chiral auxiliaries can be removed to reveal the enantiomerically pure struts $(S_p)$-1 and $(R_p)$-1. The enantiopure struts $(R_p)$-1 and $(S_p)$-1 can be incorporated into the homochiral porous frameworks of $(R_p)$-P5A-MOF-1 and $(S_p)$-P5A-MOF-1 (FIG. 2). The resultant homochiral porous frameworks are suitable for use a substrates to separate enantiomers from racemic mixtures.

Compositions and Methods of Synthesis

The synthetic protocol developed to obtain enantiomerically pure struts $(S_p)$-1 and $(R_p)$-1 (FIG. 3A) begins with pillar[5]arene ditriflate 2 that can be prepared in three steps from DMpillar[5]arene. Ditriflate 2 can be reacted with the (S)-prolinol-substituted 4-carbonylphenyl-boronic acid pinacol ester 3 in a Pd-catalyzed Suzuki reaction to produce the diastereoisomers $(SSS_p)$-4 and $(SSR_p)$-4 (FIG. 3B). This reaction proved to be slightly diastereoselective in favor of $(SSR_p)$-4. The two diastereoisomers of 4 can be easily separated on the hundreds of milligrams scale by employing normal phase silica HPLC (FIG. 3C). Single crystals of $(SSS_p)$-4 and $(SSR_p)$-4, suitable for X-ray crystallography, were obtained from the slow evaporation of $CH_2Cl_2$. The solid-state structures can be used to assign the absolute stereochemistry of the pillar[5]arenes in $(SSS_p)$-4 and $(SSR_p)$-4 since the absolute configuration of the (S)-prolinol is known. The (S)-prolinol auxiliaries in $(SSS_p)$-4 and $(SSR_p)$-4 were easily removed by alkaline amide hydrolysis to give the enantiomerically pure pillar[5]arene struts $(S_p)$-1 and $(R_p)$-1.

Figure 4A:
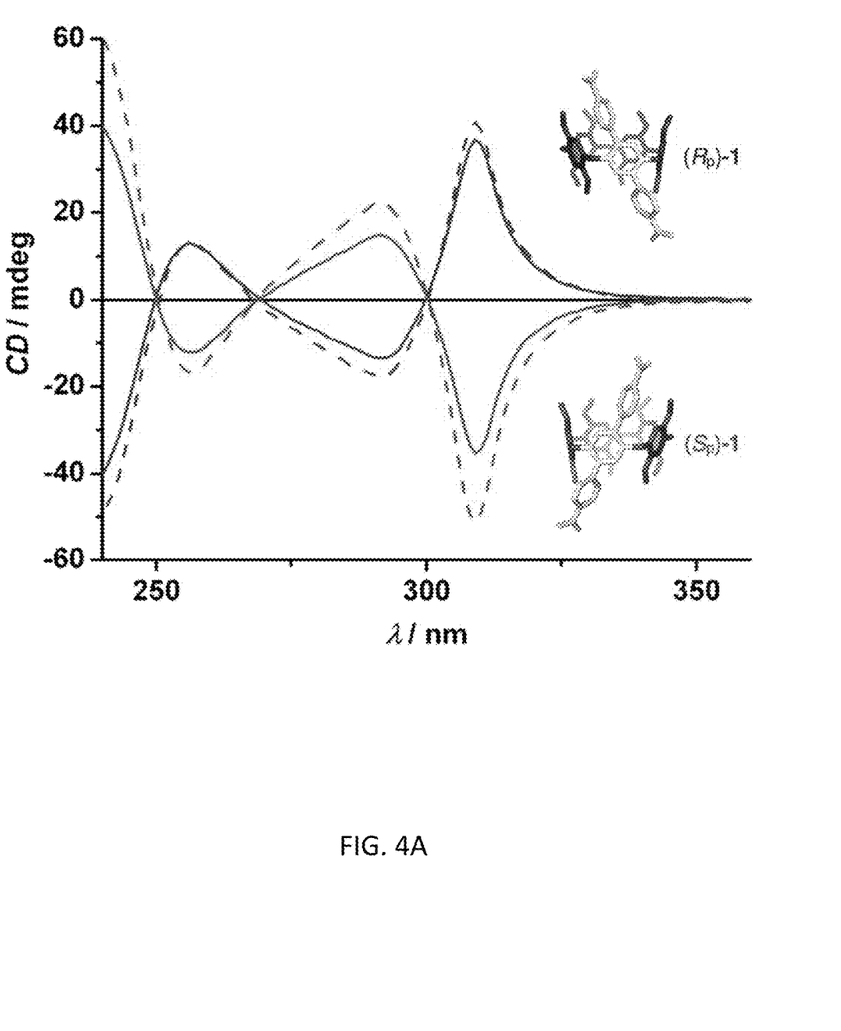
FIG. 4A depicts exemplary circular dichroism (CD) spectroscopy of $(S_p)$-1 (red) and $(R_p)$-1 (blue). The solid line spectra were collected from $(S_p)$-1 and $(R_p)$-1 (MeCN, 0.5 mM) as synthesized and the dashed line spectra were collected from digested $(S_p)$-P5A-MOF-1 (red) and $(R_p)$-P5A-MOF-1 dissolved (~0.5 mM) in MeCN.
Figure 4B:
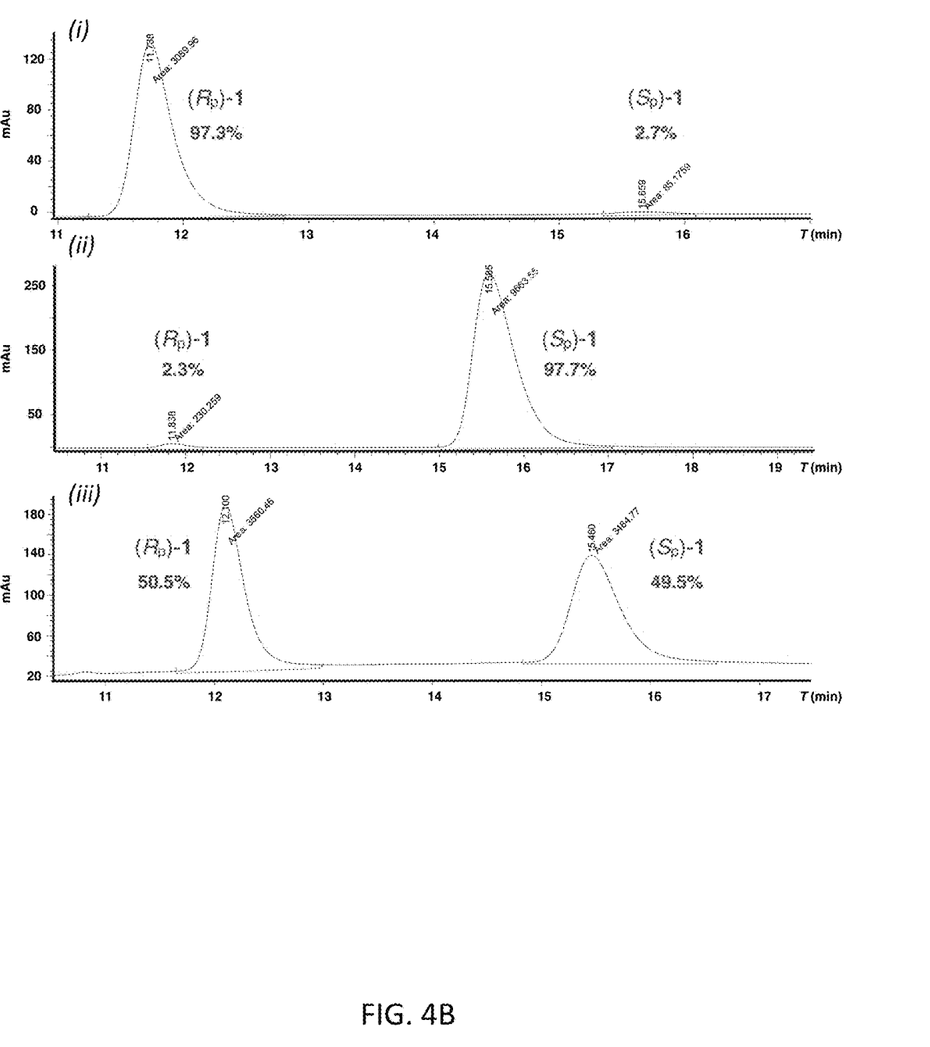
FIG. 4B depicts an exemplary analytical chiral HPLC (gradient of hexanes/iPrOH from 90:10 to 50:50 over 40 min, $\lambda$=254 nm) of samples of the resolved enantiomers $(R_p)$-1 (panel (i)), $(S_p)$-1 (panel (ii)) and the racemic mixture rac-1 (panel (iii)).

Circular dichroism (CD) spectroscopy of $(S_p)$-1 and $(R_p)$-1 (FIG. 4A) confirms that the conditions employed for amide hydrolysis do not lead to racemization of the strut. The positive Cotton effect observed for $(R_p)$-1 and the negative Cotton effect for $(S_p)$-1 agree well with the Cotton effects witnessed for enantiomerically pure pillar[5]arene derivatives. The optical purities of the methyl esters of $(S_p)$-1 and $(R_p)$-1 were assessed by analytical scale chiral HPLC (FIG. 4B) and samples of both enantiomers were shown to have enantiomeric ratios of over 97:3.

Figure 5A:
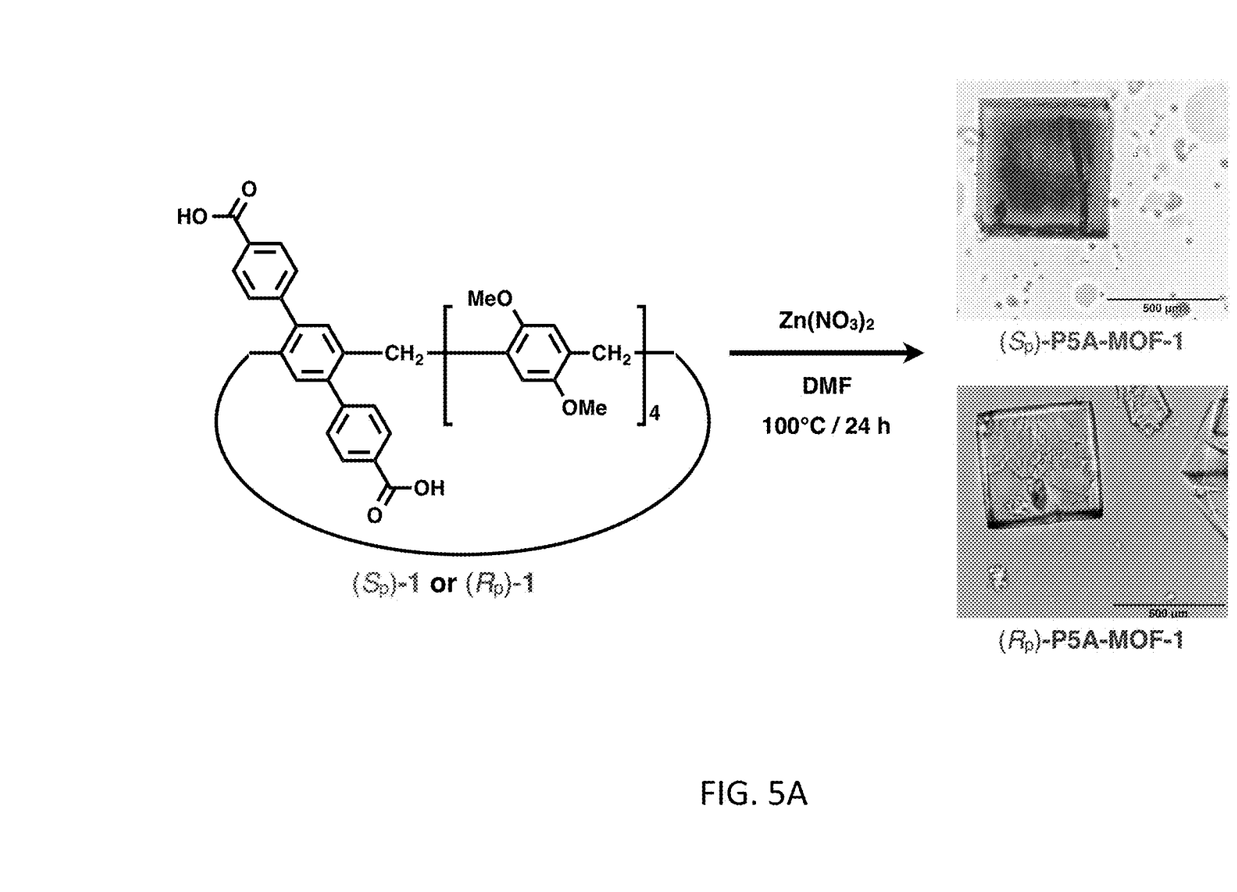
FIG. 5A depicts an exemplary synthesis of homochiral P5A-MOF-1; optical microscopy image of a crystal of $(S_p)$-P5A-MOF-1 and $(R_p)$-P5A-MOF-1 are shown.
Figure 5B:
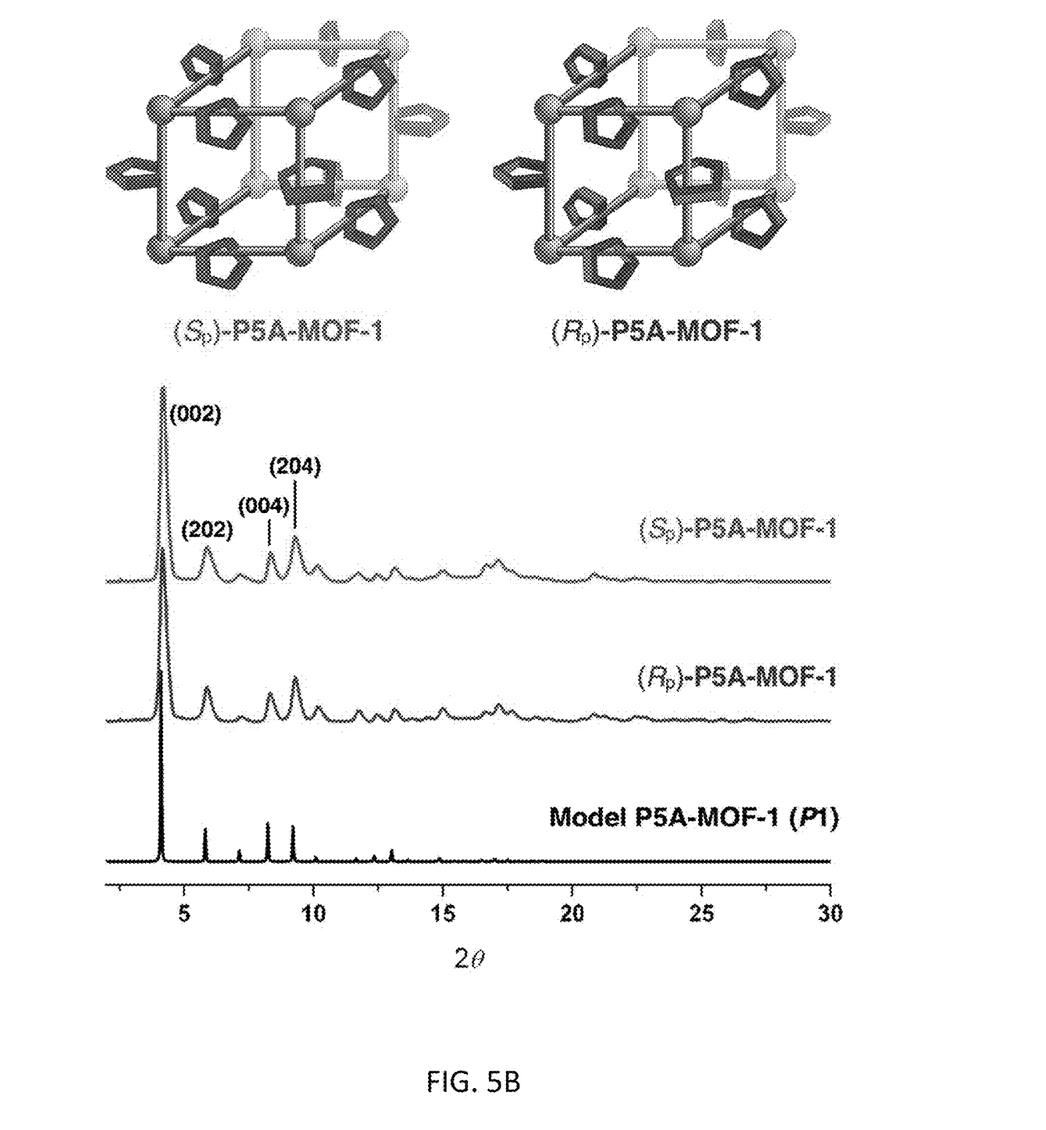
FIG. 5B depicts exemplary powder X-ray diffraction (PXRD) patterns of $(S_p)$-P5A-MOF-1 (red) and $(R_p)$-P5A-MOF-1 (blue), shown above as graphical representations, match closely those PXRD patterns of the modeled P5A-MOF-1 structure.

The homochiral frameworks $(S_p)$-P5A-MOF-1 and $(R_p)$-P5A-MOF-1 were obtained from $(S_p)$-1 and $(R_p)$-1, respectively, and $Zn(NO_3)_2 \cdot 6H_2O$ in DMF at 100° C. (See the ESI†). Crystals of (S$_p$)-P5A-MOF-1 and (R$_p$)-P5A-MOF-1 were large and cubic with approximate average volumes of 0.125 mm$^3$ (FIG. 5A) Single-crystal X-ray diffraction analysis of the homochiral MOFs were found to not be well enough resolved to discern individual atoms in the solid-state structure. In common with rac-P5A-MOF-1, the disorder within the homochiral frameworks is most likely a consequence of the rotational freedom of the pillar[5]arene rings with respect to the terphenylene linker. The powder X-ray diffraction (PXRD) patterns of (S$_p$)-P5A-MOF-1 and (R$_p$)-P5A-MOF-1 are in almost complete agreement (FIG. 5B) and match well with the PXRD pattern of the modeled version of rac-P5A-MOF-1 in a P1 space group. The PXRD data indicates that the enantiopure pillar[5]arene active domains in the homochiral frameworks do not change significantly the overall structure of the MOF. CD spectroscopy on samples of digested crystals of (S$_p$)-P5A-MOF-1 and (R$_p$)-P5A-MOF-1 (FIG. 4A) provide evidence that racemization of (S$_p$)-1 and (R$_p$)-1 does not occur at the elevated temperatures that are required for the synthesis of the MOF.

The production of homochiral MOFs that contain enantiopure pillar[5]arene active domains has been described. The resultant homochiral MOFs that contain enantiopure pillar[5]arene active domains are early examples of porous frameworks incorporating active domains that possess planar chiralities. In the preparation of these homochiral materials, an efficient route to the large-scale resolution of racemic pillar[5]arene derivatives has also been developed. The enantioselectivities of these homochiral porous frameworks towards small molecule racemates can be bound enantioselectively within the pillar[5]arene active domains.

Methods of Chiral Recognition and Enantioselective Separation

The enantiopure pore environments within (S$_p$)-P5A-MOF-1 and (R$_p$)-P5A-MOF-1 can be used in chiral recognition and enantioselective separation processes. The enantiopure (S$_p$)-P5A-MOF-1 or (R$_p$)-P5A-MOF-1 can exclusively take up one of two enantiomeric compounds from a racemic mixture. The incorporated enantiomer can be easily extracted by immersing the complex formed between the enantiomer and (S$_p$)-P5A-MOF-1 or (R$_p$)-P5A-MOF-1 in a suitable organic solvent, such as anhydrous acetone. The (S$_p$)-P5A-MOF-1 and (R$_p$)-P5A-MOF-1 maintain high crystallinity and the enantiopure pore environments can be regenerated simply by the immersion into the excess amount of a suitable organic solvent, such as anhydrous acetone.

Applications

In a first aspect a homochiral metal organic framework (MOF) is provided. The homochiral MOF selected from a group consisting of (S$_p$)-P5A-MOF-1 and (R$_p$)-P5A-MOF-1.

In a second aspect, a method of preparing a homochiral metal organic framework (MOF) consisting of (S$_p$)-P5A-MOF-1 is provided. The method includes two steps. The first step includes preparing a mixture of (S$_p$)-1 and Zn(NO$_3$)$_2$ in a solvent, wherein (S$_p$)-1 is the S$_p$-enantiomer structure of formula (I):

The second step includes heating the mixture at an elevated temperature to form the homochiral metal organic framework (MOF) consisting of (S$_p$)-P5A-MOF-1.

In a first respect of the second aspect, the solvent is anhydrous dimethylformamide. In a second respect of the second aspect, the elevated temperature is about 100° C.

In a third aspect, a method of preparing a homochiral metal organic framework (MOF) consisting of (R$_p$)-P5A-MOF-1 is provided. The method includes two steps. The first step includes preparing a mixture of (R$_p$)-1 and Zn(NO$_3$)$_2$ in a solvent, wherein (R$_p$)-1 is the R$_p$-enantiomer structure of formula (I):

The second step includes heating the mixture at an elevated temperature to form the homochiral metal organic framework (MOF) consisting of (R$_p$)-P5A-MOF-1.

In a first respect of the third aspect, the solvent is anhydrous dimethylformamide. In a second respect of the third aspect, the elevated temperature is about 100° C.

In a fourth aspect, a method of preparing a pure enantiomer structure of formula (I):

(I)

is provided. The method includes two steps. The first step includes preparing a mixture comprising an aqueous-base solution and a solvent comprising a pure enantiomer structure of formula (II):

(II)

The second step includes heating the mixture at an elevated temperature to form the pure enantiomer structure of formula (I).

In a first respect of the fourth aspect, the pure enantiomer structure of formula (I) is the $(S_p)$-1 enantiomer and the pure enantiomer structure of formula (II) is the $(SSS_p)$-4 enantiomer. In a second respect of the fourth aspect, the pure enantiomer structure of formula (I) is the $(R_p)$-1 enantiomer and the pure enantiomer structure of formula (II) is the $(SSR_p)$-4 enantiomer. In a third respect of the fourth aspect, the solvent comprises dimethoxyethane. In a fourth respect of the fourth aspect, wherein the aqueous-base solution comprises aqueous sodium hydroxide. In a fifth respect of the fourth aspect, the elevated temperature comprises at least about 85° C.

In a fifth aspect, a method of isolating an enantiomer compound from a racemic mixture is provided. The method includes two steps. The first step includes contacting the racemic mixture with a homochiral metal organic framework (MOF) selected from a group consisting of $(S_p)$-P5A-MOF-1 and $(R_p)$-P5A-MOF-1 to form a complex comprising the enantiomer compound and the homochiral MOF. The second step includes washing the complex with a solvent to remove an uncomplexed component of the racemic mixture.

In a first respect of the fifth aspect, the homochiral metal organic framework (MOF) is $(S_p)$-P5A-MOF-1. In a second respect of the fifth aspect, the homochiral metal organic framework (MOF) is $(R_p)$-P5A-MOF-1. In a third respect of the fifth aspect, the solvent is selected from an aqueous medium or an organic medium. In a fourth respect of the fifth aspect, the uncomplexed component includes an enantiomer compound from the racemic mixture.

EXAMPLES

The invention will be more fully understood upon consideration of the following non-limiting examples, which are offered for purposes of illustration, not limitation.

Example 1

Materials and Methods

Compound 2 (Strutt et al. (2012)) and 4-Iodobenzoyl chloride (Gallardo H. et al. *Synthesis,* 2008:605) were prepared using previously reported procedures. All starting materials and reagents were purchased from commercial suppliers and used without further purification. Solvents (DMF and $CH_2Cl_2$) were dried using a commercial solvent purification system (SG Water, Inc.). Analytical thin-layer chromatography (TLC) was carried out using glass plates, precoated with silica gel 60 and fluorescent indicator (Whatman LK6F). The plates were inspected by UV light (254 nm). Flash chromatography was carried out using silica gel 60 (Silicycle) as the stationary phase. 1D and 2D nuclear magnetic resonance (NMR) spectra were recorded at 298 K, unless stated otherwise, on Bruker Avance III 500 and 600 MHz spectrometers, with working frequencies of 499.373 and 600.168 MHz for $^1H$, and 125.579 and 150.928 MHz for $^{13}C$ nuclei, respectively. Chemical shifts are reported in ppm relative to the signals corresponding to the residual non-deuterated solvent and coupling constants were recorded in Hertz (Hz). All $^{13}C$ NMR spectra were recorded with the simultaneous decoupling of proton nuclei. Electrospray ionization (ESI) mass spectra were obtained on an Agilent 6210 LC-TOF high-resolution mass spectrometer. Preparative HPLC was performed on a Waters PrepLC 2000 with a Rainin Dynamax silica LC column (60 Å pore size). Analytical HPLC was performed with a Phenomenex Luna silica LC column (0.46×25 cm, 10 μm particle size, 100 Å pore size). Chiral analytical HPLC was performed with a Chiral Pak IA column (0.46×25 cm) purchased from Daicel Chemical Industries. Single crystal X-ray data was collected on a Bruker Kappa APEX CCD Diffractometer equipped with a CuKα microsource with Quazar optics. Powder patterns for MOF samples were collected on a Bruker AXS APEX2 diffractometer equipped with a CCD detector and a CuKα IμS microfocus source with MX optics. Samples were mounted in nylon cryoloops on a goniometer head. Data was collected with an area detector as rotation frames over 180° in ϕ at 2θ values of 12°, 24°, and 36° and exposed for 10 min for each frame. At a distance of 150 mm, the detector area covers 24° in 2θ. Powder pattern data were treated for amorphous background scatter. UV/Vis Absorbance spectra were recorded using a UV-3600 Shimadzu spectrophotometer. CD spectroscopy was conducted with a Jasco J-815 CD spectrometer in a 2 mm path length cuvette at 298 K. Optical microscopy images were recorded with an Olympus BX53 research microscope.

Example 2

Synthetic Protocols for Preparing $(SSS_p)$-4 and $(SSR_p)$-4

Figure 3A:
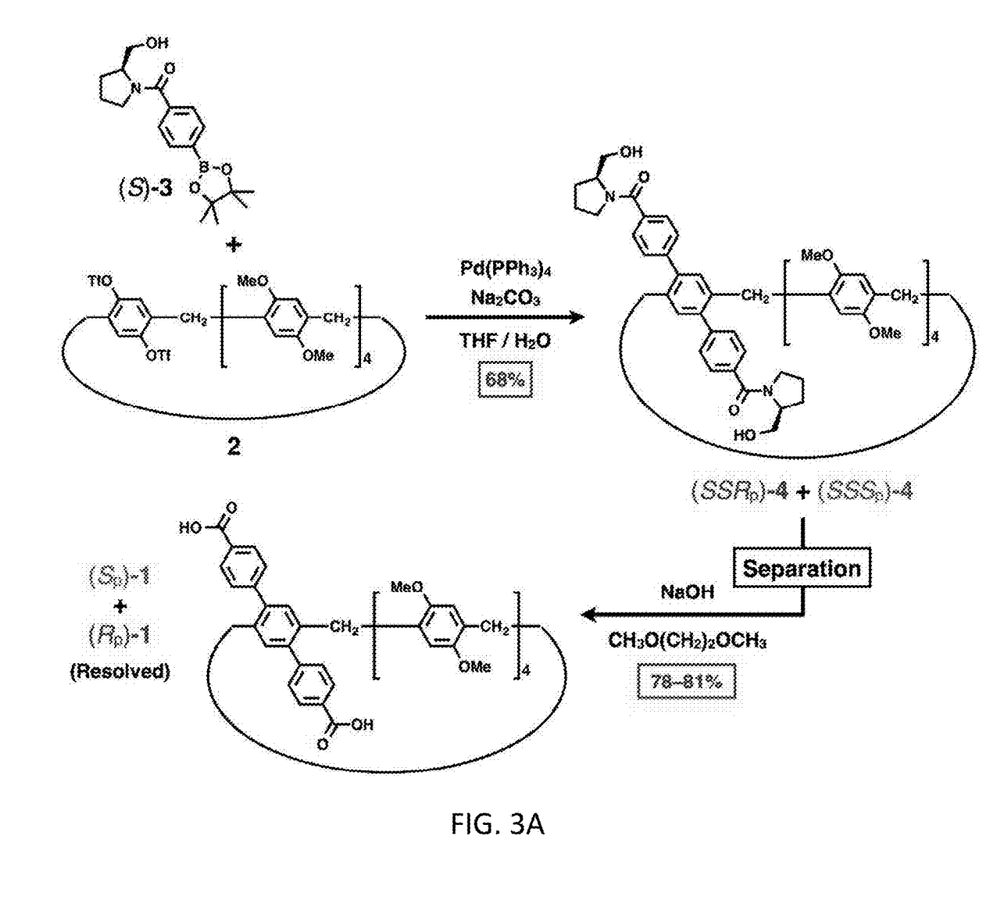
FIG. 3A depicts an exemplary scheme for the synthesis of pure enantiomers of the chiral organic strut 1, ($S_p$)-1 and ($R_p$)-1, on account of planar chirality from ditriflate 2 using chiral auxiliaries to aid the separation of the diastereoisomers of intermediate 4 (that is, ($SSS_p$)-4 and ($SSR_p$)-4).
Figure 3B:
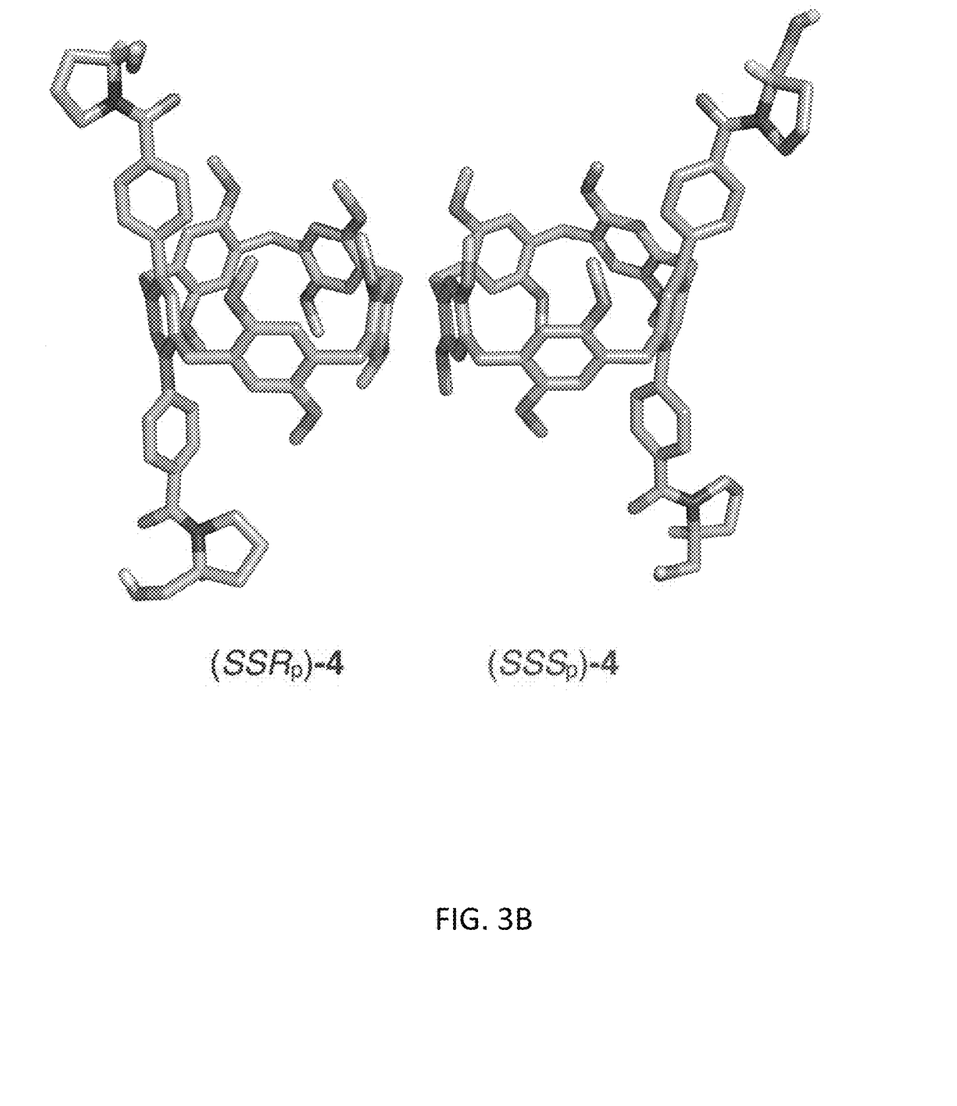
FIG. 3B depicts the solid-state structures of $(SSS_p)$-4 and $(SSR_p)$-4, wherein the C atoms are grey, O atoms are white and N atoms are blue; the H atoms have been removed for clarity.
Figure 3C:
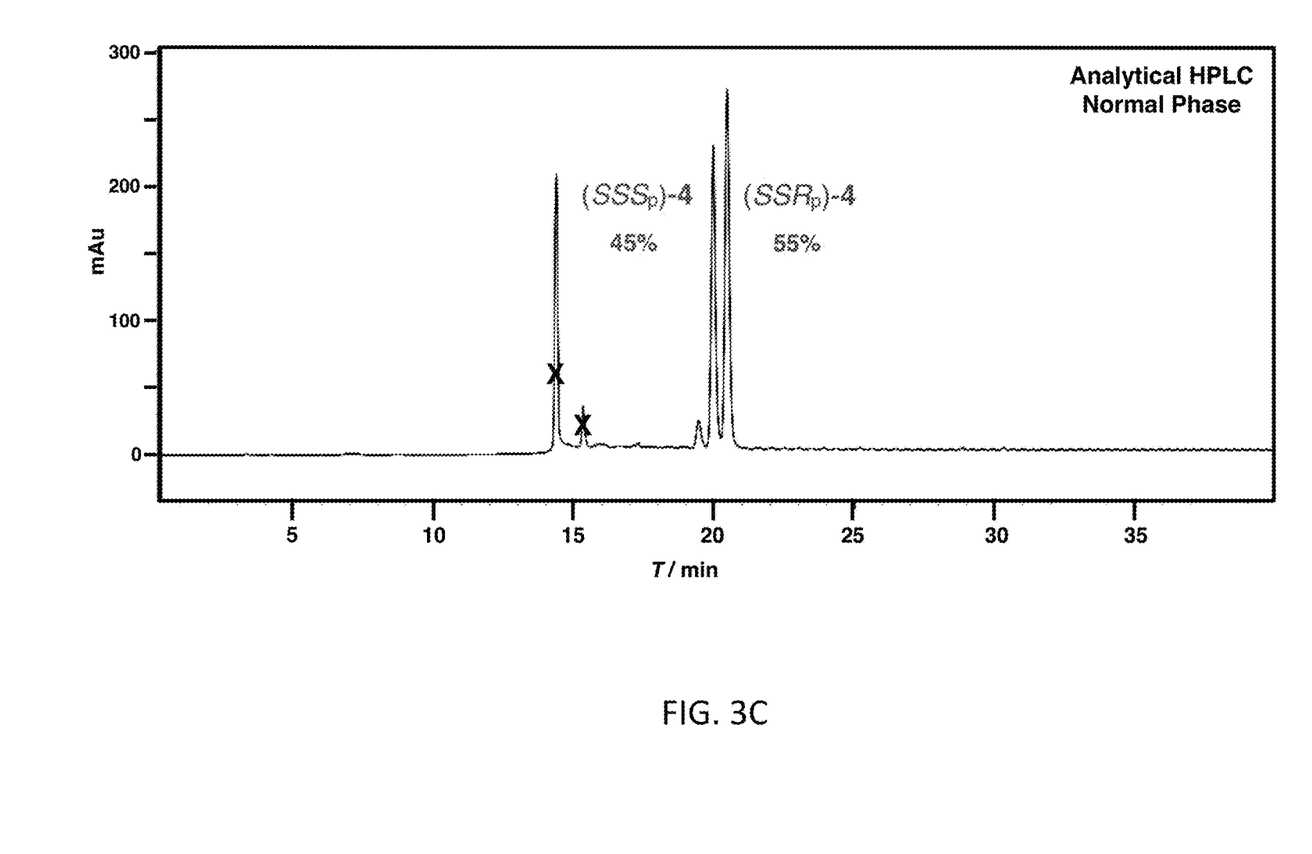
FIG. 3C depicts an exemplary analytical HPLC ($SiO_2$, gradient of $CH_2Cl_2$/MeOH from 100:0 to 94:6 over 40 min, $\lambda$=254 nm) of the diastereoisomers $(SSS_p)$-4 and $(RRR_p)$-4.

FIG. 3A provides an overview of the synthesis of $(SSS_p)$-4 and $(SSR_p)$-4.

1) (S)-6: The synthesis of (S)-6 was achieved according to Scheme (1A):

(Scheme (1A))

A solution of 4-Iodobenzoyl chloride (1.00 g, 3.75 mmol) in CH$_2$Cl$_2$ (10 mL) was added dropwise to a solution of (S)-2-Pyrrolidinemethanol (0.50 g, 4.9 mmol) and Et$_3$N (1.65 mL) in CH$_2$Cl$_2$ under nitrogen atmosphere at 0° C. The reaction mixture was warmed to rt and stirred for 16 h under nitrogen atmosphere, before being concentrated under vacuum and subjected to silica gel chromatography (gradient of CH$_2$Cl$_2$/MeOH from 100:0 to 97:3) to give (S)-6 (1.04 g, 83%). $^1$H NMR (500 MHz, CDCl$_3$, 298 K) δ=7.77 (d, J=8 Hz, 2H), 7.25 (d, J=8 Hz, 2H), 4.75 (dd, J$_1$=8 Hz, J$_2$=2 Hz, 1H), 4.38 (qd, J$_1$=8 Hz, J$_2$=2 Hz, 1H), 3.82-3.70 (m, 2H), 3.51-3.43 (m, 2H), 2.21-2.15 (m, 1H), 1.91-1.86 (m, 1H), 1.80-1.71 (m, 1H), 1.67-1.60 (m 1H). $^{13}$C NMR (125 MHz, CDCl$_3$, 298 K) δ=170.9, 137.5, 136.1, 128.8, 96.5, 66.3, 61.3, 51.1, 28.2, 25.0. HRMS: (m/z): calcd for [M+Na]$^+$: 353.9961; found 353.9964.

2) (S)-3: The synthesis of (S)-3 was achieved according to Scheme (1B):

(Scheme (1B))

[PdCl$_2$ (ddpf)] (50 mg) was added to a solution of (S)-6 (200 mg, 0.60 mmol), bis(pinacolato)diboron (450 mg, 1.8 mmol) and KOAc (180 mg, 1.8 mmol) in dry and degassed Me$_2$SO (50 mL). The reaction mixture was heated to 70° C. and stirred for 16 h before being cooled to RT and extracted with CH$_2$Cl$_2$ (200 mL), and washed with H$_2$O (200 mL). The aqueous phase was washed twice with CH$_2$Cl$_2$ (100 mL). The combined organic phases were washed with H$_2$O, dried with NaSO$_4$, concentrated under vacuum and subjected to silica gel chromatography (gradient of CH$_2$Cl$_2$/MeOH from 100:0 to 98:2) to give (S)-3 (160 mg, 80%). $^1$H NMR (500 MHz, CDCl$_3$, 298 K) δ=7.84 (d, J=8 Hz, 2H), 7.48 (d, J=8 Hz, 2H), 4.98 (bs, 1H), 4.39 (qd, J$_1$=8 Hz, J$_2$=2 Hz, 1H), 3.82-3.71 (m, 2H), 3.48-3.42 (m, 2H), 2.20-2.14 (m, 1H), 1.88-1.83 (m, 1H), 1.77-1.71 (m, 1H), 1.66-1.58 (m, 1H), 1.35 (s, 12H). $^{13}$C NMR (125 MHz, CDCl$_3$, 298 K) δ=172.3, 139.1, 134.8, 126.2, 84.2, 75.1, 67.4, 61.7, 51.2, 28.7, 25.0, 24.7. HRMS: (m/z): calcd for [M+Na]$^+$: 353.1883; found 353.1885.

3) $(SSS_p)$-4 and $(SSR_p)$-4: The syntheses of $(SSS_p)$-4 and $(SSR_p)$-4 were achieved according to Scheme (1C):

(Scheme (1C))

-continued (SSS$_p$)-4/(SSR$_p$)-4

Pd(PPh$_3$)$_4$ (300 mg) was added to a mixture of 2 (1.00 g, 1.01 mmol), (S)-3 (1.00 g, 3.05 mmol) and aqueous Na$_2$CO$_3$ (650 mg in 25 mL) in THF (100 mL). The mixture was stirred at 80° C. for 24 h, cooled to room temperature and added to CH$_2$Cl$_2$ (300 mL). The solution was washed with H$_2$O (2×100 mL) and brine (100 mL), and dried (Na$_2$SO$_2$), concentrated under vacuum, and subjected to silica gel chromatography (gradient of CH$_2$Cl$_2$/MeOH from 100:0 to 95:5) to give a mixture of (SSS$_p$)-4 and (SSR$_p$)-4. The mixture of diastereoisomers was then subjected to HPLC (silica, gradient of CH$_2$Cl$_2$/MeOH from 100:0 to 94:6 over 40 min, λ=254 nm) to yield pure (SSS$_p$)-4 (340 mg, 31%) and (SSR$_p$)-4 (410 mg, 37%).

Characterization of (SSS$_p$)-4: $^1$H NMR (500 MHz, CDCl$_3$, 298 K) δ=7.49 (d, J=8 Hz, 4H), 7.15 (d, J=8 Hz, 4H), 7.12 (s, 2H), 6.77 (s, 2H), 6.71 (s, 2H), 6.51 (s, 2H), 5.87 (s, 2H), 4.45 (q, J=8 Hz, 2H), 3.90-3.55 (m, 18H), 3.68 (s, 6H), 3.55 (s, 6H), 3.36 (s, 12H), 2.28-2.19 (m, 2H), 1.98-1.91 (m, 2H), 1.86-1.77 (m, 2H), 1.72-1.62 (m, 2H). $^{13}$C NMR (125 MHz, CDCl$_3$, 298 K) δ=172.3, 151.2, 151.1, 150.8(3), 150.7(5), 144.4, 139.9, 136.6, 134.9, 132.4, 129.5, 129.1, 128.9, 128.4, 127.8, 127.1, 114.5, 114.3, 114.1, 114.0, 67.8, 61.9, 56.2, 56.1, 55.6, 51.4, 33.2, 30.1, 29.6, 28.8, 25.3.

Characterization of (SSR$_p$)-4: $^1$H NMR (500 MHz, CDCl$_3$, 298 K) δ=7.48 (d, J=8 Hz, 4H), 7.13 (d, J=8 Hz, 4H), 7.09 (s, 2H), 6.77 (s, 2H), 6.71 (s, 2H), 6.53 (s, 2H), 5.87 (s, 2H), 4.47 (q, J=8 Hz, 2H), 3.89-3.64 (m, 18H), 3.69 (s, 6H), 3.59 (s, 6H), 3.38 (s, 6H), 3.34 (s, 6H), 2.27-2.19 (m, 2H), 1.98-1.91 (m, 2H), 1.84-1.77 (m, 2H), 1.71-1.63 (m, 2H). $^{13}$C NMR (125 MHz, CDCl$_3$, 298 K) δ=172.1, 151.0, 150.9, 150.6(4), 150.6(1), 144.4, 139.8, 136.5, 134.8, 132.3, 129.4, 128.9, 128.8, 128.4, 127.7, 127.0, 114.3(1), 114.2(6), 114.0, 113.9, 67.3, 61.6, 56.2, 56.1, 55.9, 55.6, 51.4, 33.0, 30.0, 29.5, 28.6, 25.2.

HRMS for (SSS$_p$)-4/(SSR$_p$)-4: (m/z): calcd for [M+H]$^+$: 1097.5158; found 1097.5150.

Example 3

Synthetic Protocols for Preparing (S$_p$)-1 and (R$_p$)-1

FIG. 3A provides an overview of the synthesis of (S$_p$)-1 and (R$_p$)-1.

The synthesis of (S$_p$)-1 and (R$_p$)-1 was achieved according to Scheme (2A):

(Scheme 2A)

(SSS$_p$)-4/(SSR$_p$)-4

(S$_p$)-1/(R$_p$)-1

(S$_p$)-1 and (R$_p$)-1: An aqueous solution of NaOH (1.0 g in 10 mL H$_2$O) was added to a solution of either (SSS$_p$)-4 or (SSR$_p$)-4 (200 mg, 0.18 mmol) in dimethoxyethane (20 mL). The reaction mixture was stirred at 85° C. for 4 d before being cooled to rt, added to H$_2$O (100 mL), acidified with concentrated HCl (12.4 M, 10 mL) and extracted with EtOAc (2×100 mL). The combined organic layers were washed with H$_2$O, dried with Na$_2$SO$_4$, dried under vacuum to yield (S$_p$)-1 (135 mg, 81%) or (R$_p$)-1 (130 mg, 78%). The NMR spectra and mass were identical to those reported (Strutt et al. (2012)) for the racemic compound rac-1. $^1$H NMR (500 MHz, (CD$_3$)$_2$CO, 298 K) δ=11.31 (bs, 2H), 8.08 (d, 4H, J=8.5 Hz), 7.37 (d, 4H, J=8 Hz), 7.36 (s, 2H), 7.23 (s, 2H), 6.91 (s, 2H), 6.83 (s, 2H), 6.68 (s, 2H), 5.87 (s, 2H), 3.89 (d, 2H, J=13.5 Hz), 3.85 (d, 2H, J=14 Hz), 3.79 (s, 2H), 3.77 (s, 6H), 3.72 (s, 6H), 3.70 (d, 2H, J=13 Hz), 3.64 (d, 2H, 13 Hz), 3.52 (s, 6H), 3.41 (s, 6H). $^{13}$C NMR (125 MHz, (CD$_3$)$_2$CO, 298 K) δ=167.6, 151.6, 151.5, 151.2, 151.0, 148.1, 140.6, 137.2, 133.1, 130.6, 130.3, 129.9, 129.3, 129.0, 128.1, 114.7, 114.3, 114.2, 113.8, 56.1, 56.0, 55.7, 55.5, 33.0. HRMS: (m/z): calcd for [M+Na]$^+$: 953.3507; found 953.3507.

Example 4

Synthetic Protocols for Preparing (S$_p$)-5 and (R$_p$)-5

The synthesis of (S$_p$)-5 and (R$_p$)-5 was achieved according to Scheme (2B):

(Scheme (2B))

LiOH (10 mg) was added to a solution of either ($S_p$)-1 ($R_p$)-1 or the racemic compound rac-1 (10 mg, 0.01 mmol) in THF (10 mL) and the reaction mixture was stirred at rt for 30 min. $Me_2SO_4$ (0.1 mL) was then added to the reaction mixture and the reaction mixture was brought to reflux and stirred for 16 h, before being concentrated under vacuum and subjected to silica gel chromatography (gradient of $CH_2Cl_2$/MeOH from 100:0 to 96:4) to give either ($S_p$)-5 (5 mg, 50%) or ($R_p$)-5 (6 mg, 60%). The $^1H$ and $^{13}C$ NMR spectra and mass were identical to those reported (Strutt et al. (2012)) for the racemic compound rac-1. $^1H$ NMR (500 MHz, $CDCl_3$, 298 K) δ=7.97 (d, 4H, J=8 Hz), 7.15 (d, 4H, J=8 Hz), 7.08 (s, 2H), 6.82 (s, 2H), 6.75 (s, 2H), 6.58 (s, 2H), 5.86 (s, 2H), 3.99 (s, 6H), 3.88(2) (d, 2H, J=14.5 Hz), 3.87(9) (s, 2H), 3.82 (d, 2H, J=14 Hz), 3.77 (d, 2H, J=13.5 Hz), 3.74 (s, 6H), 3.72 (d, 2H, J=13.5 Hz), 3.63 (s, 6H), 3.40 (s, 6H), 3.36 (s, 6H). $^{13}C$ NMR (125 MHz, $CDCl_3$, 298 K) δ=167.2, 151.1(1), 151.0(6), 150.8, 150.6, 147.2, 140.0, 136.6, 132.2, 129.6, 129.4, 129.0, 128.5, 127.5, 128.4, 114.4, 114.0(0), 113.9(8), 113.8, 56.1, 55.7, 55.5, 53.5, 52.3, 33.3, 30.1, 29.7. HRMS: (m/z): calcd for $[M+NH_4]^+$: 976.4286; found 976.4267.

Example 5

MOF Synthesis

Homochiral P5A-MOF-1 was prepared by heating a mixture of either ($S_p$)-1 or ($R_p$)-1 (20 mg) and $Zn(NO_3)_2 \cdot 6H_2O$ (20 mg) in anhydrous DMF (2.5 mL) at 100° C. for 24 h. Optical microscopy image of a crystal of ($S_p$)-P5A-MOF-1 and ($R_p$)-P5A-MOF-1 is presented in FIG. 5A.

Example 6

X-Ray Crystallography ($SSS_p$)-4:

a) Methods. Single crystals of ($SSS_p$)-4 were grown by slow evaporation of $CH_2Cl_2$.

Data was collected at 100 K on a Bruker Kappa APEX CCD Diffractometer equipped with a $CuK_\alpha$ microsource with Quazar optics. The structure was twinned, and thus Twinabs was used to generate hkl files. The SQUEEZE function of PLATON was used to remove the contribution of disordered solvent molecules. The total solvent accessible volume/cell=1,148 Å$^3$ [19.5%] and the total electron count/cell=230. Although the exact solvent content is not known, this total electron count/cell equates to approximately six $CH_2Cl_2$ molecules. Only the atoms used in the refinement model are reported in the formula here.

b) Crystal Parameters. $[(C_{67}H_{72}N_2O_{12})_2 \cdot CH_2Cl_2]$. Colorless plates (0.015×0.146×0.237 mm). Monoclinic, $P2_1$, a=12.0918(5), b=21.3853(9), c=26.0509(12) Å, α=90.000, β=92.817(3), γ=90.000°, V=6728.3(5) Å$^3$, Z=2, T=100(2) K, ρcalc=1.125 g/cm$^3$, μ=0.972 mm$^{-1}$. Flack x parameter=0.12(4), determined by classical intensity fit. Of a total of 10925 reflections that were collected, 10925 were unique (Rint=0.0000). Final $R_1(F^2>2\sigma F^2)$=0.0824 and wR2=0.2421 (all). The structure was solved by direct methods and expanded using Fourier techniques. CCDC #995695.

($SSR_p$)-4:

a) Methods. Single crystals of ($SSR_p$)-4 were grown by slow evaporation of $CH_2Cl_2$.

Data was collected at 100 K on a Bruker Kappa APEX CCD Diffractometer equipped with a $CuK_\alpha$ microsource with Quazar optics. The solvent masking procedure as implemented in Olex2 was used to remove the electronic contribution of solvent molecules from the refinement. The total solvent accessible volume/cell=637.2 Å$^3$ [19.5%] and the total electron count/cell=161.2. Although the exact solvent content is not known, this total electron count/cell equates to approximately four $CH_2Cl_2$ molecules. Only the atoms used in the refinement model are reported in the formula here.

b) Crystal Parameters. $[C_{67}H_{72}N_2O_{12}]$. Colorless plates (0.011×0.09×0.173 mm). Monoclinic, $P2_1$, a=12.9346(2), b=11.7299(1), c=21.685(3) Å, α=90.000, β=97.077(9), γ=90.000°, V=3265.1(7) Å$^3$, Z=2, T=100(2) K, ρcalc=1.116 g/cm$^3$, μ=0.616 mm$^{-1}$. Flack x=0.1(6) parameter, determined using 989 quotients. Of a total of 12576 reflections that were collected, 6172 were unique ($R_{int}$=0.0939). Final $R_1(F^2>2\sigma F^2)$=0.0922 and wR$_2$=0.2501. The structure was solved by direct methods and expanded using Fourier techniques. CCDC #995696.

References

Strutt N L, Zhang H, Stoddart J F, "Enantiopure pillar[5]arene active domains within a homochiral metal-organic framework," *Chem Commun* (*Camb*) 50:7455-8 (2014).

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A method of preparing a homochiral metal organic framework (MOF) consisting of ($S_p$)-P5A-MOF-1, comprising:

preparing a mixture of ($S_p$)-1 and $Zn(NO_3)_2$ in a solvent, wherein ($S_p$)-1 is the $S_p$-enantiomer structure of formula (I):

and heating the mixture at temperature of about 100° C. to form the homochiral metal organic framework (MOF) consisting of ($S_p$)-P5A-MOF-1.

2. The method of claim 1, wherein the solvent is anhydrous dimethylformamide.

3. A method of preparing a homochiral metal organic framework (MOF) consisting of ($R_p$)-P5A-MOF-1, comprising:
preparing a mixture of ($R_p$)-1 and $Zn(NO_3)_2$ in a solvent, wherein ($R_p$)-1 is the $R_p$-enantiomer structure of formula (I):

(I)

and
heating the mixture at temperature of about 100° C. to form the homochiral metal organic framework (MOF) consisting of ($R_p$)-P5A-MOF-1.

4. The method of claim 3, wherein the solvent is anhydrous dimethylformamide.

5. A method of preparing a pure enantiomer structure of formula (I):

(I)

comprising:
preparing a mixture comprising an aqueous-base solution and a solvent comprising a pure enantiomer structure of formula (II):

(II)

heating the mixture at temperature of about 85° C. to form the pure enantiomer structure of formula (I).

6. The method of claim 5, wherein the pure enantiomer structure of formula (I) consists of the ($S_p$)-1 enantiomer and the pure enantiomer structure of formula (II) consists of the ($SSS_p$)-4 enantiomer.

7. The method of claim 5, wherein the pure enantiomer structure of formula (I) consists of the ($R_p$)-1 enantiomer and the pure enantiomer structure of formula (II) consists of the ($SSR_p$)-4 enantiomer.

8. The method of claim 5, wherein the solvent is dimethoxyethane.

9. The method of claim 5, wherein the aqueous-base solution is an aqueous sodium hydroxide.

* * * * *